(12) United States Patent
Benton

(10) Patent No.: US 10,568,766 B2
(45) Date of Patent: Feb. 25, 2020

(54) MECHANICALLY HEATED/COOLED AIR SYSTEM FOR WELDING HELMET

(71) Applicant: David Benton, Cicero, NY (US)

(72) Inventor: David Benton, Cicero, NY (US)

( * ) Notice: Subject to any disclaimer, the term of this patent is extended or adjusted under 35 U.S.C. 154(b) by 232 days.

(21) Appl. No.: 15/834,909

(22) Filed: Dec. 7, 2017

(65) Prior Publication Data

US 2019/0175412 A1 Jun. 13, 2019

(51) Int. Cl.

| | | |
|---|---|---|
| *A47J 39/00* | (2006.01) | |
| *F25B 29/00* | (2006.01) | |
| *A61F 9/06* | (2006.01) | |
| *A62B 9/00* | (2006.01) | |
| *F24F 1/022* | (2019.01) | |
| *F24F 1/04* | (2011.01) | |
| *F24F 11/30* | (2018.01) | |
| *F24F 13/28* | (2006.01) | |
| *F24F 3/16* | (2006.01) | |
| *B01D 46/00* | (2006.01) | |
| *A42B 3/28* | (2006.01) | |

(52) U.S. Cl.
CPC .............. *A61F 9/068* (2013.01); *A62B 9/006* (2013.01); *F24F 1/022* (2013.01); *F24F 1/04* (2013.01); *F24F 11/30* (2018.01); *A42B 3/285* (2013.01); *B01D 46/0005* (2013.01); *B01D 46/0086* (2013.01); *F24F 3/1603* (2013.01); *F24F 13/28* (2013.01); *F24F 2221/125* (2013.01); *F24F 2221/38* (2013.01)

(58) Field of Classification Search
CPC .... F25B 29/00; F25B 29/003; A41D 13/0053; A62B 17/005; A62B 9/006; A61F 9/068; B01D 46/0005; B01D 46/0086; F24F 2221/125; F24F 2221/38; F24F 3/1603; F24F 13/28; F24F 11/30; F24F 1/04; F24F 1/022; A42B 3/285
USPC .................................... 165/58, 65, 104.17
See application file for complete search history.

(56) References Cited

U.S. PATENT DOCUMENTS

| | | | |
|---|---|---|---|
| 3,283,520 A | | 11/1966 | Donohue et al. |
| 3,496,703 A | | 2/1970 | MacLeod |
| 4,450,900 A | * | 5/1984 | Nathan ............... B60H 1/00257 165/42 |
| 4,506,511 A | | 3/1985 | Cameto et al. |
| 4,513,580 A | * | 4/1985 | Cooper ................. F25B 29/003 62/183 |
| 4,549,541 A | | 10/1985 | Sundahl |

(Continued)

*Primary Examiner* — Amy R Weisberg
(74) *Attorney, Agent, or Firm* — Bernhard P. Molldrem, Jr.

(57) ABSTRACT

A mechanical refrigeration and heating unit supplies filtered air that is heated or chilled as needed for one or more welding helmets. A portable or transportable cabinet or housing has an air inlet on which a cartridge air filter is mounted. The air passes through an evaporator coil into an evaporator plenum where an evaporator fan moves the air to an outlet that connects with a heater plenum that contains an electric heater module. An outlet of the heater if fitted with an outlet port to which an air hose may be connected. A compressor, condenser coil, receiver, and condenser fan are located in an equipment compartment in the housing. A control board in the unit allows the user to select heated or chilled air. A clogged-filter alarm provides visual and audio alarm signals when pressure in the evaporator plenum falls below a threshold.

15 Claims, 10 Drawing Sheets

(56) References Cited

U.S. PATENT DOCUMENTS

| | | | | |
|---|---|---|---|---|
| 4,629,482 A | * | 12/1986 | Davis | B01D 46/0005 |
| | | | | 55/385.2 |
| 4,888,958 A | * | 12/1989 | Ella | A61F 7/00 |
| | | | | 62/237 |
| 4,890,335 A | | 1/1990 | Crowson | |
| 4,901,538 A | * | 2/1990 | Anthony | B64D 9/00 |
| | | | | 454/77 |
| 4,905,475 A | | 3/1990 | Tuomi | |
| 4,971,052 A | | 11/1990 | Edwards | |
| 5,031,690 A | * | 7/1991 | Anderson | B60H 1/3226 |
| | | | | 165/43 |
| 5,062,424 A | * | 11/1991 | Hooker | A41D 13/0053 |
| | | | | 128/897 |
| 5,085,267 A | * | 2/1992 | Torrence | B60H 1/00885 |
| | | | | 165/204 |
| 5,193,347 A | * | 3/1993 | Apisdorf | A42B 3/285 |
| | | | | 2/171.3 |
| 5,353,605 A | * | 10/1994 | Naaman | A41D 13/0053 |
| | | | | 2/171.3 |
| 5,572,880 A | * | 11/1996 | Frustaci | A62B 7/06 |
| | | | | 128/201.21 |
| 5,967,225 A | | 10/1999 | Jenkins | |
| 6,167,714 B1 | * | 1/2001 | Baffes | F25B 13/00 |
| | | | | 62/188 |
| 6,405,549 B1 | * | 6/2002 | Baffes | F25B 13/00 |
| | | | | 62/188 |
| 8,015,970 B2 | | 9/2011 | Klun et al. | |
| 8,104,094 B2 | | 1/2012 | Uttrachi | |
| 8,297,070 B2 | | 10/2012 | Pryor | |
| 8,336,113 B2 | | 12/2012 | Uttrachi | |
| 2003/0024529 A1 | * | 2/2003 | Beizndtsson | A62B 17/005 |
| | | | | 128/201.29 |
| 2004/0094289 A1 | * | 5/2004 | Harshberger | F24F 1/027 |
| | | | | 165/48.1 |
| 2006/0021375 A1 | * | 2/2006 | Wetzel | F24F 3/161 |
| | | | | 62/419 |
| 2008/0250800 A1 | * | 10/2008 | Wetzel | F24F 1/022 |
| | | | | 62/179 |
| 2011/0187123 A1 | * | 8/2011 | Hamm | B65D 47/02 |
| | | | | 290/1 A |
| 2013/0305438 A1 | * | 11/2013 | Fuhr | A41D 13/0051 |
| | | | | 2/458 |
| 2015/0260422 A1 | * | 9/2015 | Baruch | F24F 5/0035 |
| | | | | 62/89 |
| 2017/0136268 A1 | | 5/2017 | Boffey | |
| 2018/0070659 A1 | * | 3/2018 | Xu | A41D 31/065 |

\* cited by examiner

MECHANICALLY HEATED/COOLED AIR SYSTEM FOR WELDING HELMET

BACKGROUND OF THE INVENTION

This invention relates to portable heating and air conditioning systems, and is particularly concerned with a portable or transportable unit that can deliver heated or cooled and filtered air to headgear of a worker, e.g., the helmet worn by a welder.

At the present time, welders working in a hostile environment need to be provided with fresh filtered air delivered via a flexible air hose to their mask or helmet. In some environments where welding is performed, the welder may become unbearably warm, with temperatures often well over 100° F. In an outdoor winter environment, the welder may need to work in sub-zero surroundings, and the constant cold makes it difficult to work.

Currently, there are systems to provide air to welders masks and welders helmets, but these do not provide properly heated and filtered air or refrigerated and filtered air. Accordingly, welders working in a hostile environment, i.e., extreme heat or extreme cold, have had difficulty in working continuously due to the discomfort in the heat or cold.

Accordingly there is a need for a mechanical refrigeration/heating system that provides filtered and heated or chilled air, as needed, via an air hose to a welder's helmet. Such a unit should be electrically powered from an available source, such as the local AC mains, and the unit should be designed so that it can be wheeled by one person into the area where needed, outdoors or indoors.

OBJECTS AND SUMMARY OF THE INVENTION

Accordingly, it is an object of the invention to provide welders or other similarly situated workers with a source of filtered and temperature adjusted air, which avoids the drawbacks of the prior art.

It is an object to provide a helmet air supply system that combines refrigeration and heating so that air that is properly treated for the given environment is provided, i.e., filtered and heated air or filtered and cooled air, as needed.

It is another object to provide a single unit that can furnish either heated air or chilled air to the welder (or welders) via a hose fitted to the welder's helmet.

It is another object to provide a heated or chilled air unit that can have interchangeable single or multiple air outlet fittings so that it can be used to supply air to a single welder, two welders, or several welders.

It is another object to provide a heated or chilled air supply unit that can be wheeled into place, and in which the filter can be easily changed out.

In accordance with an aspect of this invention, a mechanically heated/cooled air system is adapted for supplying air to a welding helmet. A housing of the system has exterior walls and interior walls that define at least an evaporator plenum and an equipment compartment within the housing. The evaporator plenum has an air inlet opening in an exterior wall of the housing (e.g., the top wall) and an evaporator pan within the cabinet and beneath the air inlet opening such that the evaporator plenum is defined between the air inlet opening and the evaporator pan. An air filter, e.g., a cylindrical HEPA cartridge filter is mounted above the air inlet opening.

An evaporator coil is positioned within the evaporator plenum and an evaporator fan is positioned on or at the evaporator pan. The evaporator fan has an inlet open to the evaporator plenum and an outlet port. A heater plenum has an inlet positioned on the outlet port of the evaporator fan, a heater chamber, and an outlet port positioned at an opening in an exterior wall of the housing. A heater module is positioned within the heater chamber of the heater plenum.

The mechanical refrigeration system within the equipment compartment has a condenser coil mounted at a condenser air intake opening formed in an exterior wall of the housing. A compressor has a suction port connected to an outlet port of the evaporator coil and a pressure port connected to an inlet port of the condenser coil. A receiver member is connected to an outlet of the condenser coil. A condenser fan within the equipment compartment has an inlet open to the equipment compartment and an outlet positioned at a condenser air exhaust opening in an exterior wall of the housing. A thermal expansion valve is situated between an outlet of the receiver member and an inlet of the evaporator coil. A control board regulates power outputs connected with the compressor and with the heater module for selectively energizing one or the other of the compressor and the heater module such that the system provides filtered and heated or cooled air at the outlet port of the heater plenum. An air hose connector is positioned at the outlet port of the heater plenum and protrudes out of one wall of the housing. This air hose connector can be single or dual, i.e., it can have one or two tubular connectors for connecting helmet air hoses for one or two welding helmets.

The air filter arrangement on the air inlet opening of the preferred embodiment has a self-centering filter mount for holding the cylindrical cartridge filter. The filter mount may be pyramidical in shape having an apex at its upward end. The filter arrangement favorably also has a protective cover or filter guard.

Also favorably, a pressure switch located within the evaporator plenum is coupled to an alarm circuit, such that a predetermined low pressure in the plenum causes the alarm circuit to generate a clogged-filter alarm signal. The alarm feature generates both an audible alarm sound and a visual alarm, e.g. flashing light.

In a preferred embodiment the housing is arranged vertically, with the evaporator plenum situated on top, above the equipment compartment. The housing can have a handle member affixed onto an upper portion of the housing. The handle member can have a transverse grip bar. Favorably a pair of wheels or rollers are mounted at a lower end or base of the housing.

In a preferred embodiment the heater plenum inlet port and associated heater plenum outlet port are of tubular shape, and the heater plenum is in the form of a box containing the heater module, with tapered ends that narrow to the heater plenum inlet and heater plenum outlet ports.

The control board is favorably configured to control the power supplied to the heater module and to the compressor, such that only one or the other of the heater module and the compressor is energized at a given time.

The refrigeration and heating elements can be powered with standard 120 volt, 60 Hz AC power, or can be powered from a mobile power source.

The above and many other objects, features, and advantages of this invention will become apparent to persons skilled in the art from the ensuing description of a preferred embodiment, which should be considered in connection with the accompanying Drawing.

DETAILED DESCRIPTION OF A PREFERRED EMBODIMENT

Figure 1:
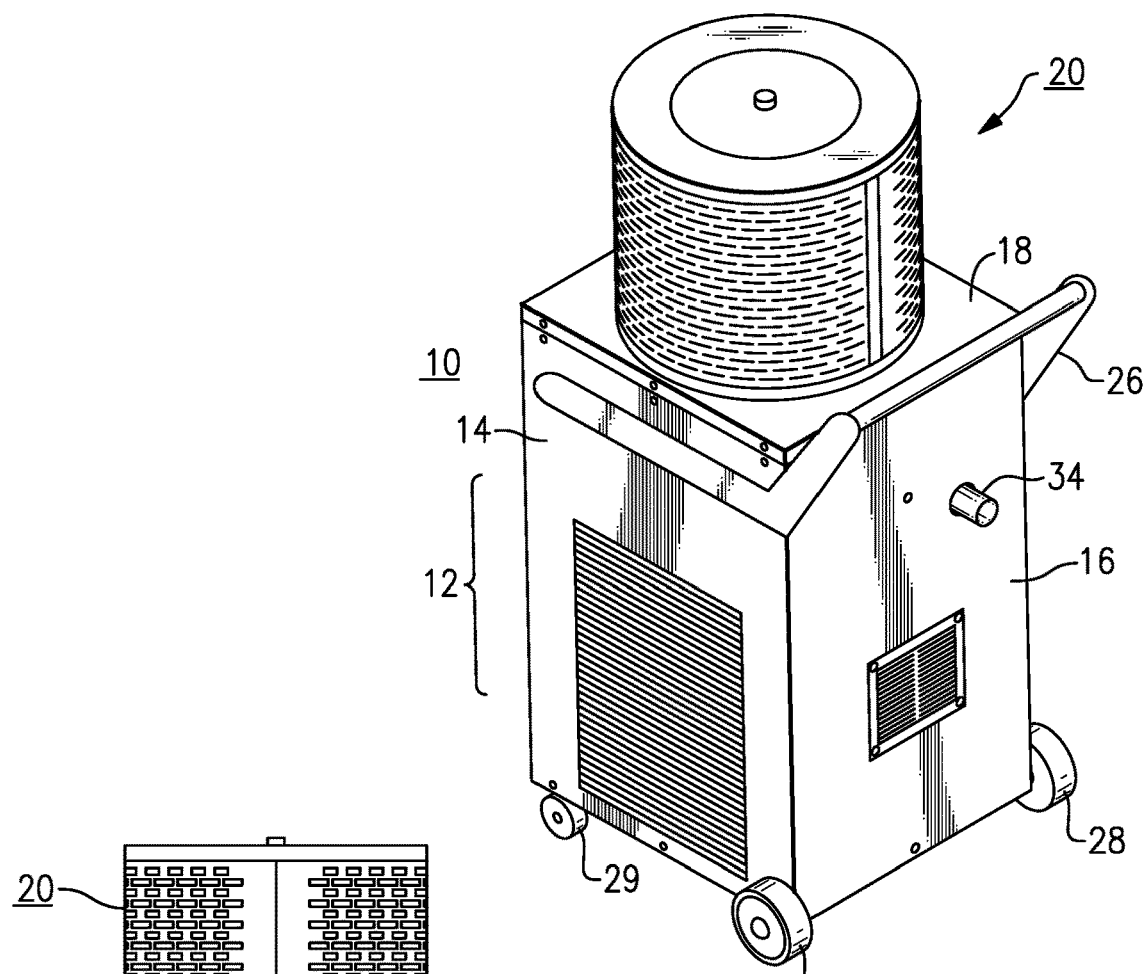
FIG. 1 is a perspective view of a mechanical cooled or heated filtered air supply unit for a welding helmet according to an embodiment of this invention.
Figure 2:
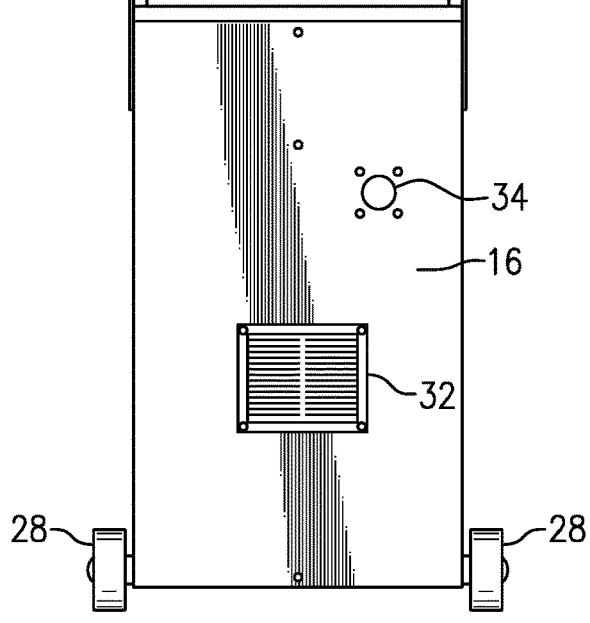
FIG. 2 is a rear elevation thereof.
Figure 3:
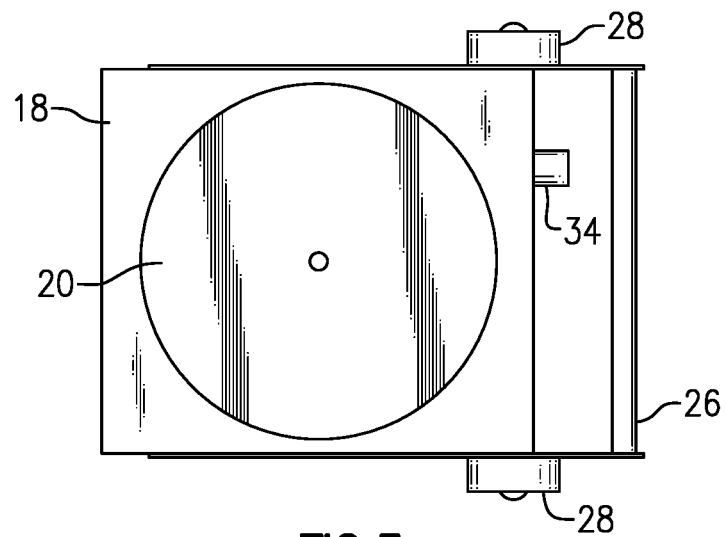
FIG. 3 is a top plan view thereof.
Figure 4:
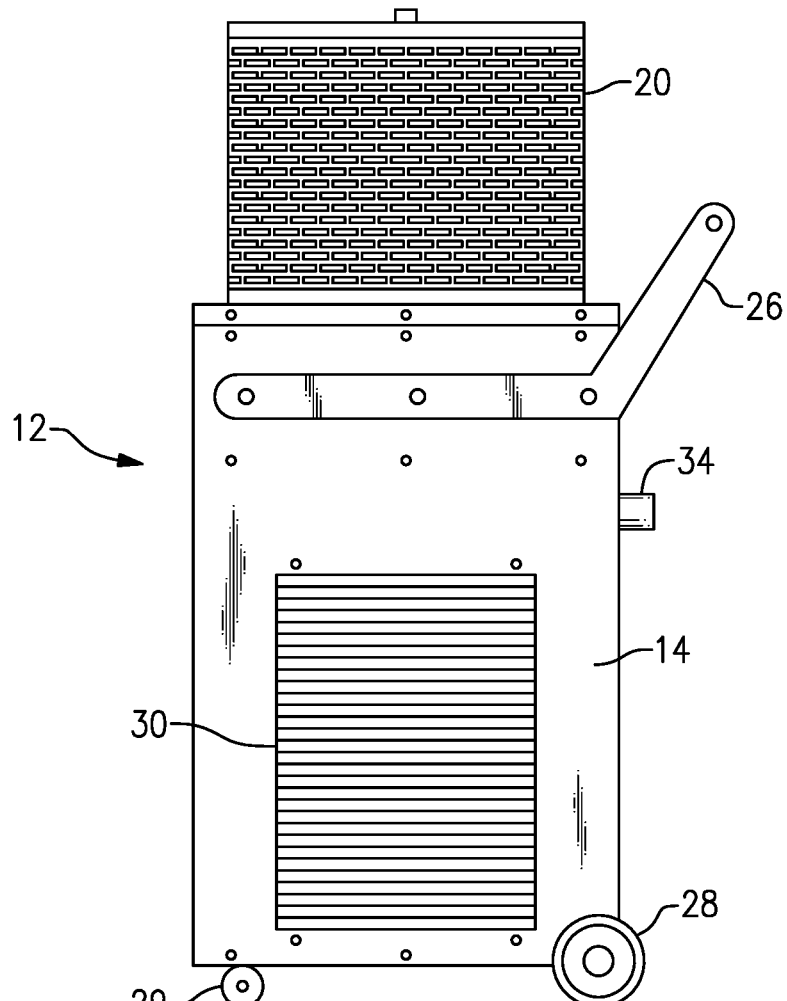
FIG. 4 is a side elevation thereof.

With reference to the Figures of Drawing, and initially to FIGS. 1 to 4 thereof, a helmet air filtering and conditioning unit 10 has a generally rectangular housing 12 formed of several external walls including a side wall 14 and a rear wall 16 as well as a top wall 18. A filter unit 20 is seated on the top wall 18 and includes a generally cylindrical filter guard or cover 22 within which is a HEPA cartridge filter 24 (see FIG. 6). A handle 26 for pulling or pushing the unit 10 has a pair of arms that project out from the two sides of the housing 12, and a tubular handle bar is situated between the outer ends of the two arms. Wheels or rollers 28 are here mounted at the bottom or base of the housing 12, at the rear, and there are a pair of caster wheels 29 at the front. The caster wheels 29 are capable of pivoting 360 degrees about the vertical axis.

Figure 5:
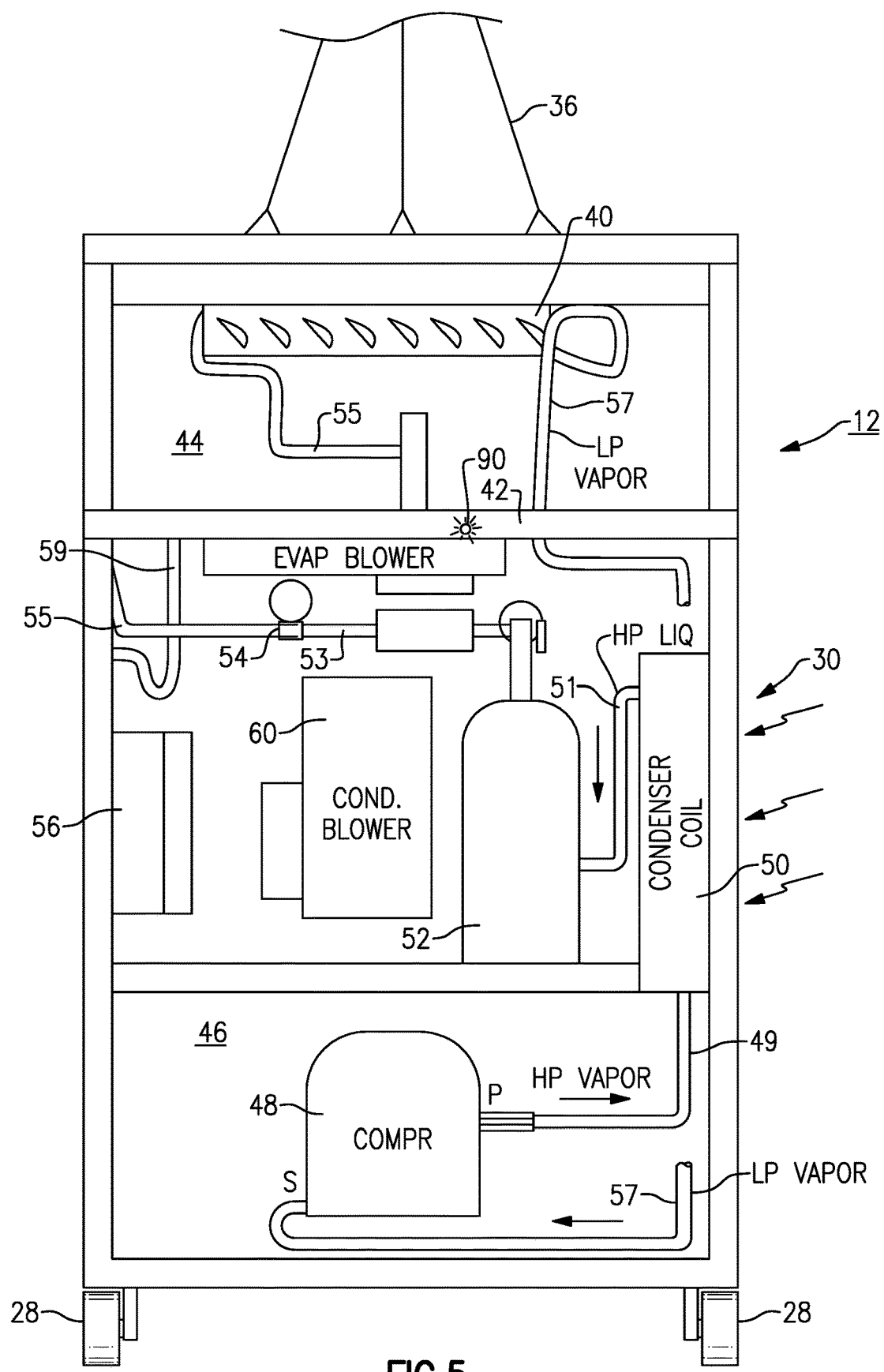
FIG. 5 is an elevation of this embodiment, with a front panel removed and showing component parts within the housing.
Figure 6:
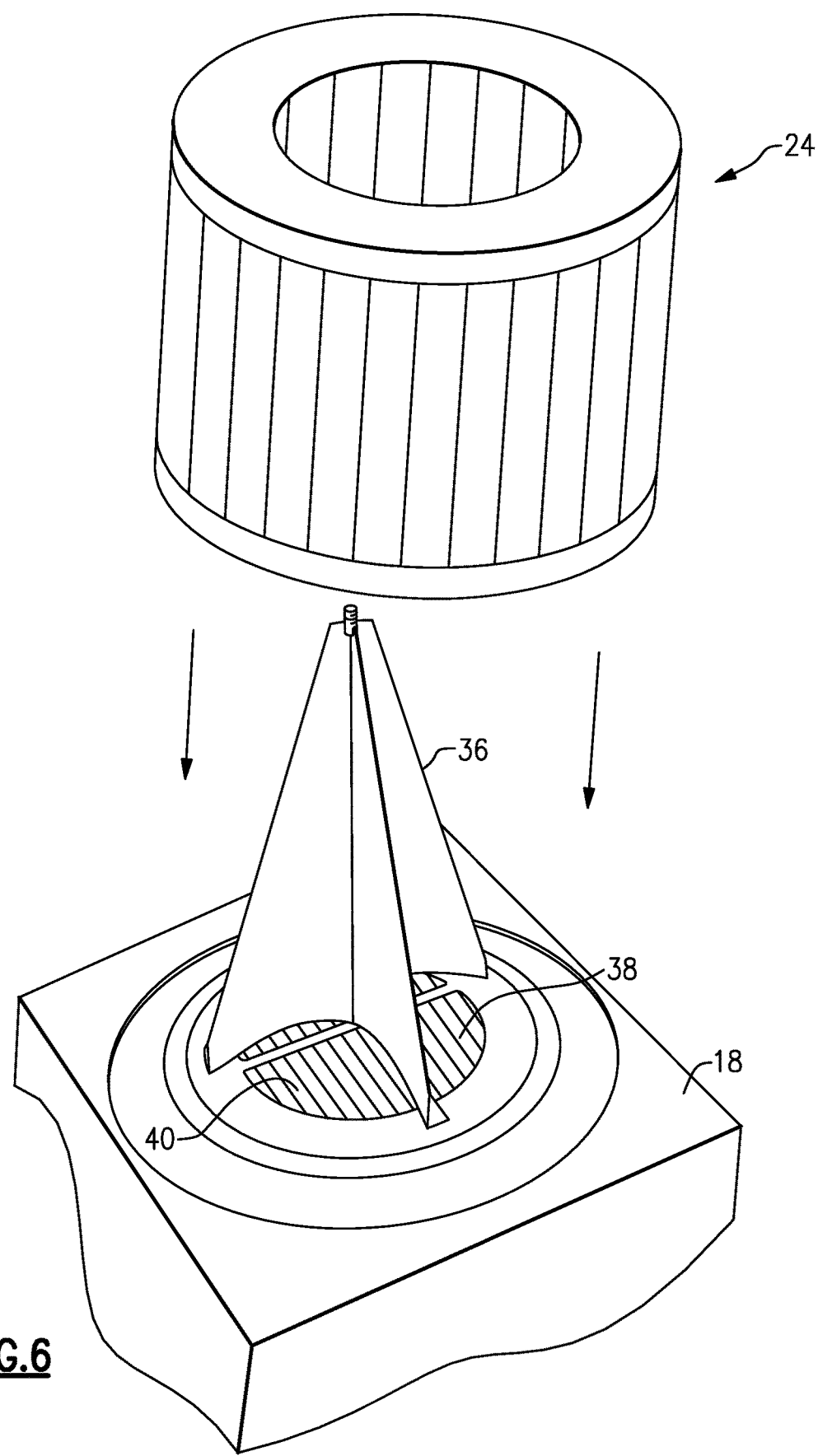
FIG. 6 is an exploded perspective of a top of this embodiment showing the air filter and filter mount.

A condenser air inlet grille 30 is shown formed in one side wall 14, and a condenser air discharge grille 32 is situated in the back wall 16. A helmet air outlet port 34 is shown projecting out through an opening is the rear wall 16. As shown in FIGS. 5 and 6, a filter cartridge holder 36 is situated at an evaporator air inlet port 38, here a round opening with the evaporator coil 40 visible in this view through the inlet port 38. In this case, the filter holder 36 has a generally pyramidical or "Christmas tree" shape, here formed of four triangular plates with the apex at the top. There is a threaded rod or similar fastener at the top or apex of the filter holder 36. This extends vertically through a small bolt hole at the center of the top disk of the cover 20 to secure the cover and filter cartridge 24 in place.

FIG. 5 shows the unit 10 with a front cover removed, such that the mechanical refrigeration system inside the housing 12 can be seen. An evaporator pan 42 is spaced a predetermined distance below the top wall 18 of the housing, where the evaporator coil 40 and evaporator air inlet port 38 are located. The top wall 18 and the evaporator pan 42 define an evaporator plenum 44. An equipment chamber or equipment compartment 46 is defined between this evaporator pan 42 and the base of the housing 12. An evaporator blower 58 is mounted on the evaporator pan 42, here at the underside thereof, with an intake port 38 (FIG. 6) at the top side, opening to the evaporator plenum 44. Air is chilled when the mechanical refrigeration system is operating and is drawn from the plenum 44 and is discharged (through the wall 16) to the helmet air outlet port 34, as will be described. Any condensation is drained through a condensation tube 59 and can be discharged out of the unit in known fashion.

Within the equipment compartment 46 is located a compressor 48 with a suction port S and pressure port P, where low pressure warm vapor refrigerant is drawn into the port S and high pressure hot vapor is discharged from the port P to a high pressure vapor line 49 that leads to a condenser coil 50 that is mounted onto the inside of the wall 14 at the location of the condenser air intake grille 30. From the condenser a high pressure liquid line 51 leads to a receiver or receiver/dryer tank 52 which serves as a reservoir for pressurized liquid refrigerant. A high pressure liquid line 53 then leads from the receiver 52 to a thermally controlled expansion valve 54 which provides low pressure liquid through a low-pressure liquid line 55 to the evaporator. A low-pressure vapor line 57 then brings the low pressure refrigerant gas back to the suction port S of the compressor 48.

A condenser air blower 60 is mounted at the inside of the wall 16 with its outlet port at the location of the condenser air discharge grille 32 (as shown in FIG. 1)

A control board 56 is positioned inside the equipment compartment 46 to control power that is applied to the compressor 48, blowers 58, 60, and other equipment inside the housing 12.

Figure 7:
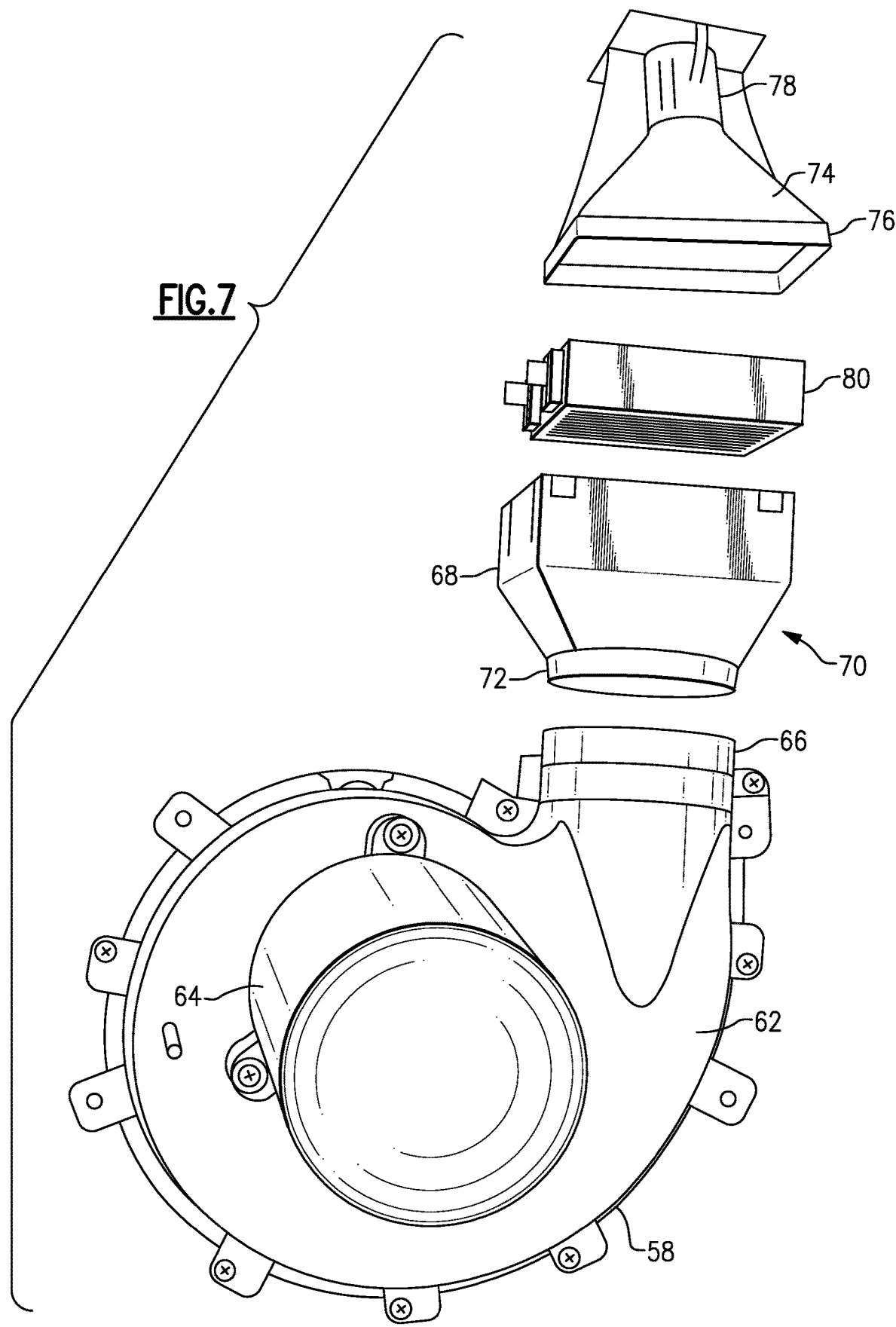
FIG. 7 is an exploded assembly view of the evaporator fan, heater plenum and heater module in this embodiment.
Figure 8:
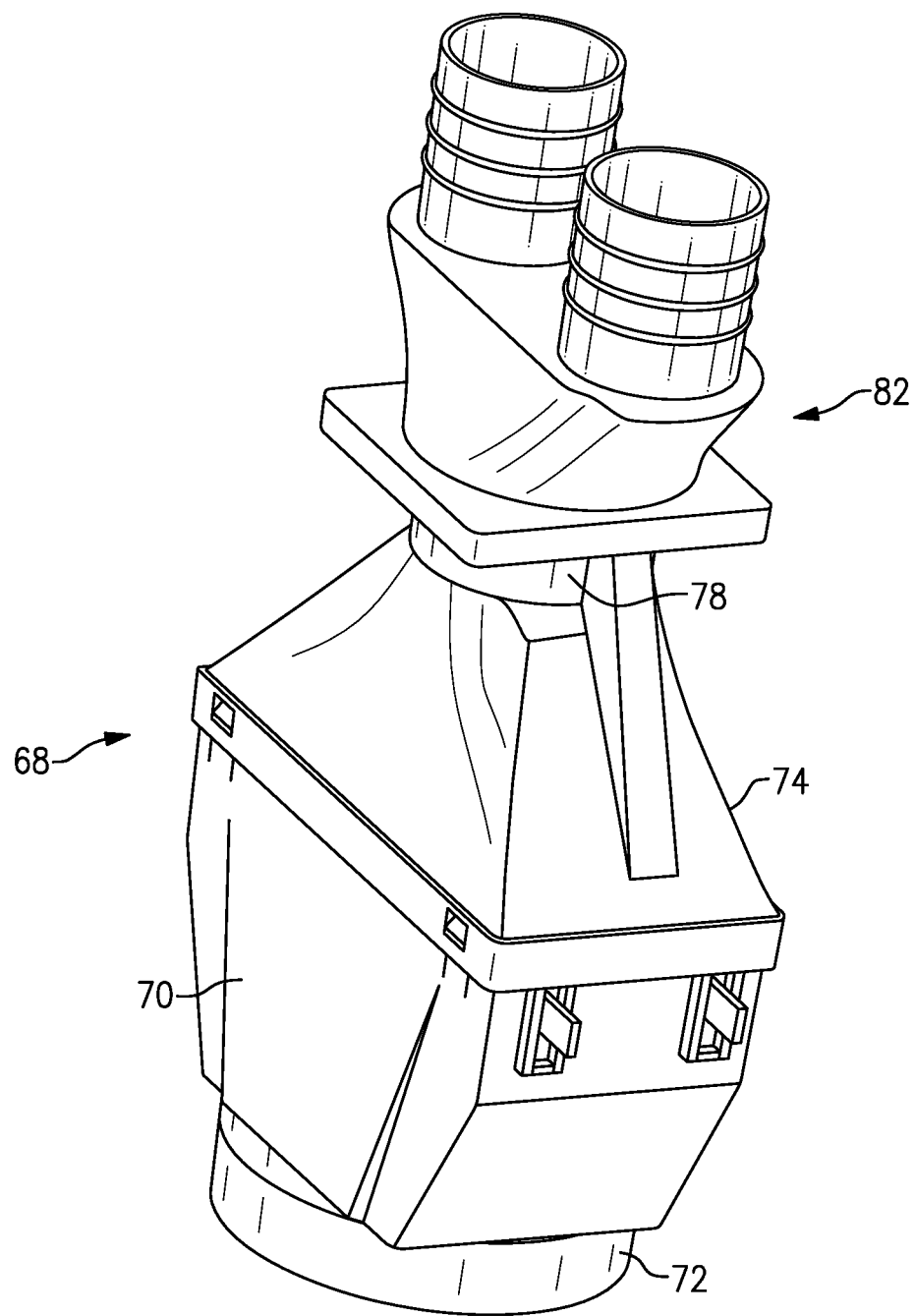
FIG. 8 is a perspective view of an assembled heater plenum and module, with a dual connector.
Figure 9:
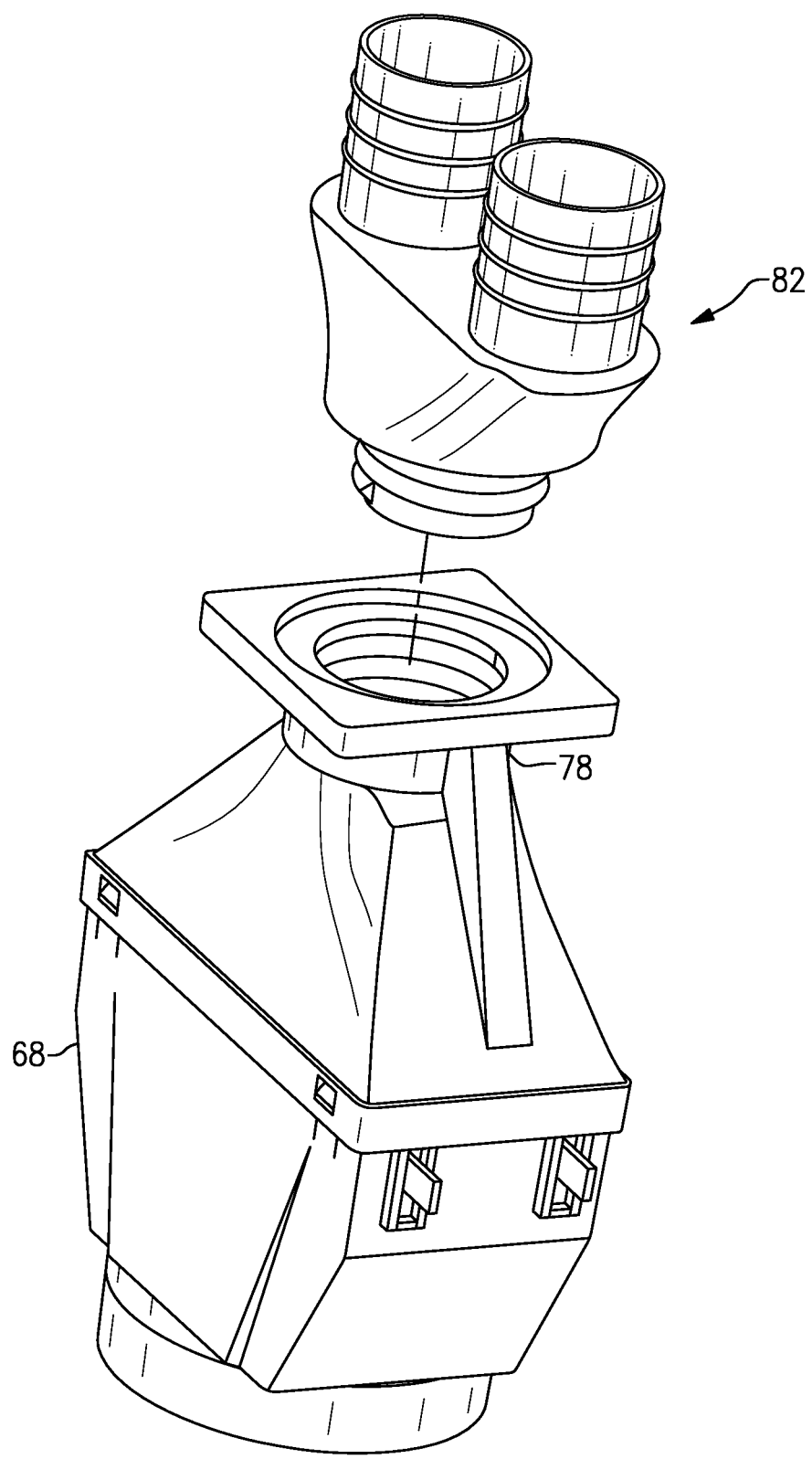
FIG. 9 is a partly exploded assembly view thereof.
Figure 10:
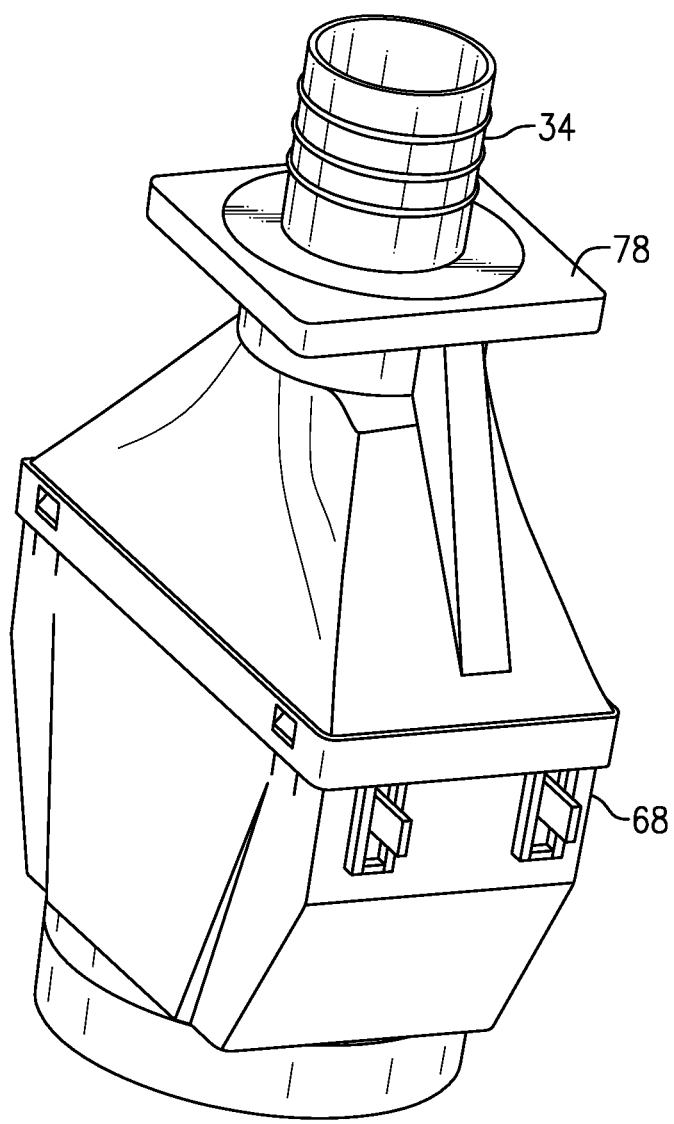
FIG. 10 is a perspective view of an assembled heater plenum and module, with a single hose connector.
Figure 11:
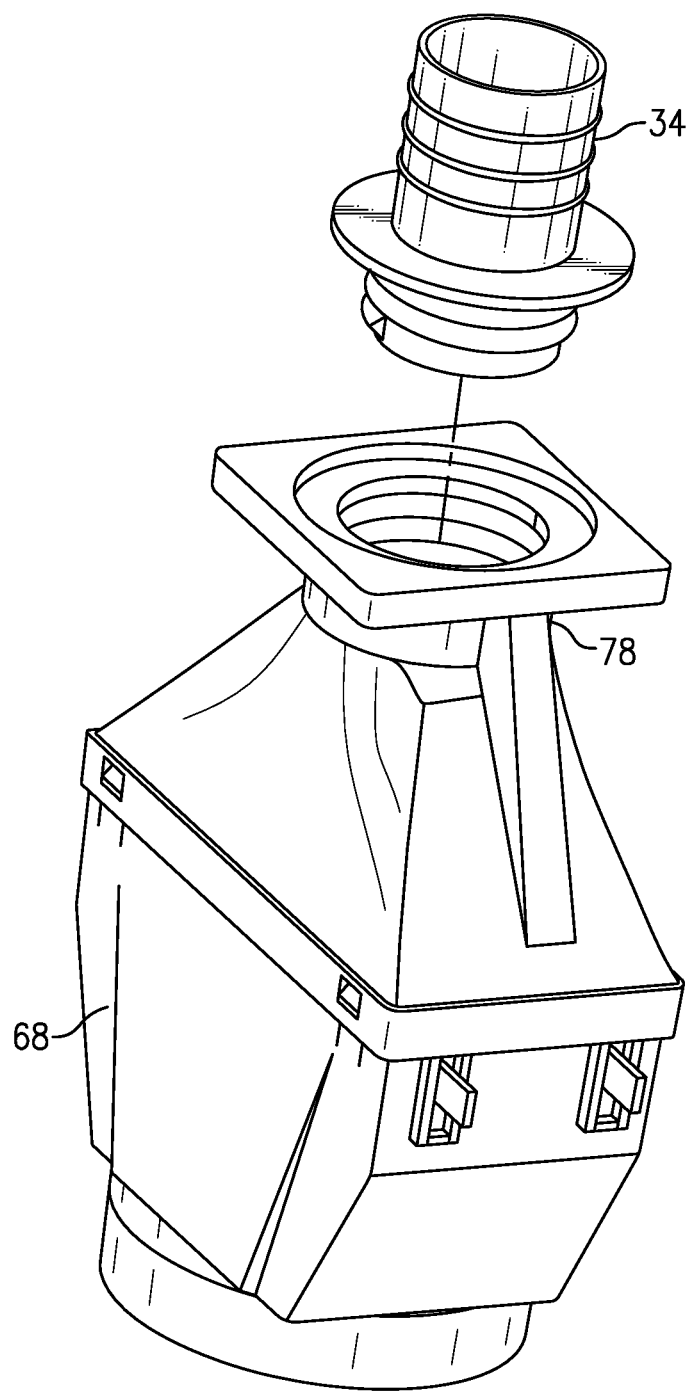
FIG. 11 is a partly exploded assembly view thereof.

The evaporator fan 58 or blower, and associated heating mechanism for alternatively supplying chilled air or heated air to the welding helmet, are shown in FIG. 7 as an assembly view. The blower 58 is here shown as a centrifugal blower with a housing 62 and associated motor 64. The housing 62 has a cylindrically shaped exhaust port 66. A heater assembly is comprised of a heater plenum 68 formed of a generally rectangular box 70 with a inlet portion that tapers down to a fitting ring 72 that mates with the exhaust port 66 of the fan 58. A heater block 80 is dimensioned to fit within the box 70 of the plenum 68. The heater block has a pair of electrodes that fit through slots in one wall of the plenum 68 and these connect to electrical conductors for powering the heater block 80. An end cover 74 for the heater plenum has a rectangular flange 76 that seats onto the distal end of the heater plenum 68 to enclose the heater block 80. The end cover 74 tapers down and leads to a tubular member 78 to which a plug-in hose connector (34 or 82) can be inserted. As shown in FIGS. 8 and 9 a plug-in connector module 82 can be fitted into the member 78, a dual arrangement for connecting to two welding helmets via a pair of air hoses. This can interlock to remain in place, or it can be permanently installed. A similar arrangement is shown in FIGS. 10 and 11 but with a plug-in module 32 that has a single outlet tube, and which is used when the unit 10 is to adapted to supply air to a single welding helmet.

Air for the welding helmet(s) first passes through the HEPA filter 24 and through the inlet port 38 and evaporator coil 40 into the evaporator plenum 44. The evaporator blower 58 forces the air from the evaporator plenum through the heater plenum 68 and heater block 80 and this air exits out through the exit port or connector 34 or 82. Where heated air is needed the compressor is turned off and the heater block 80 is energized, but when chilled air is needed the compressor is energized and the heater block 80 is turned off.

Figure 12:
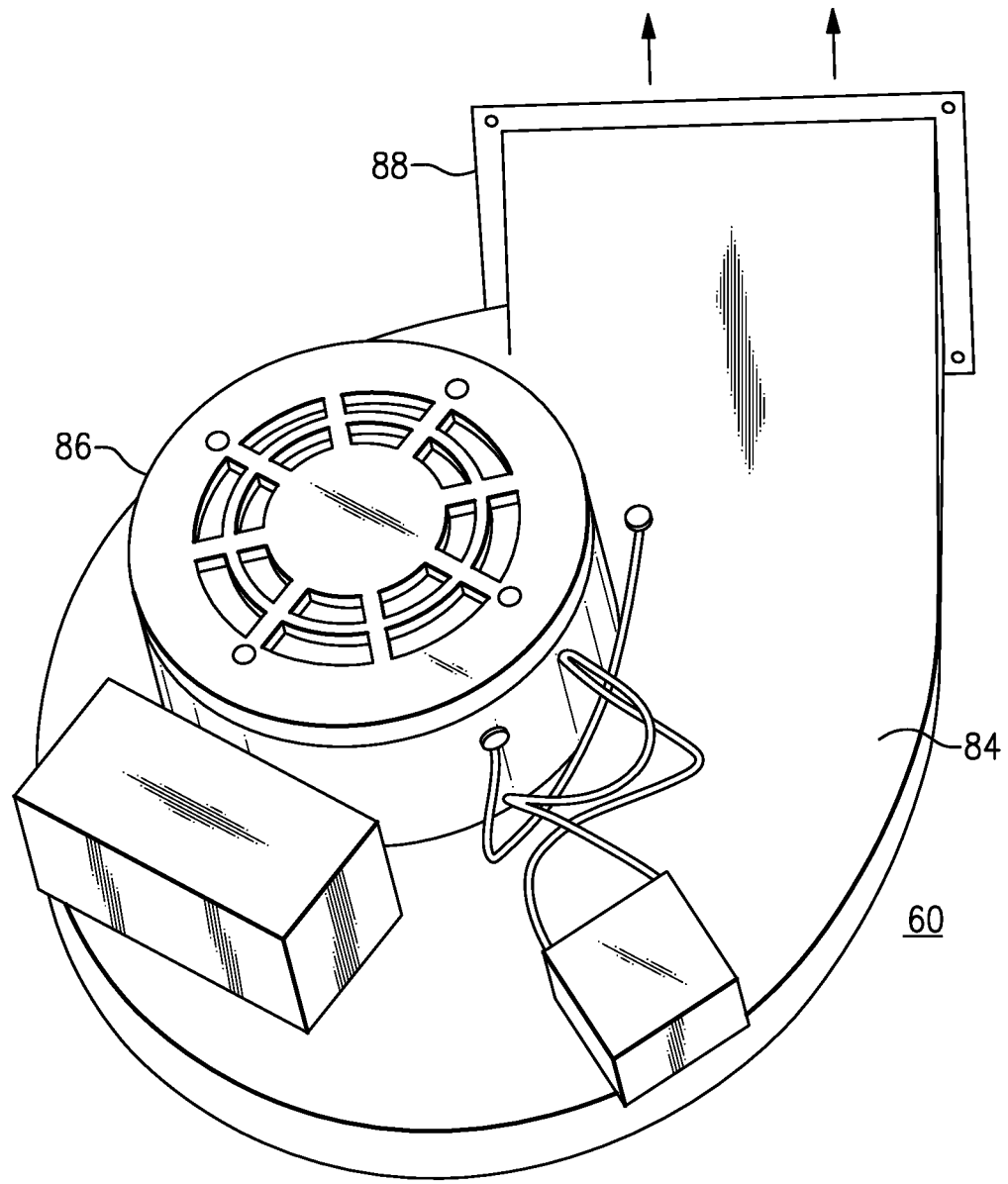
FIG. 12 is a perspective view of the condenser air fan as employed in this embodiment.

An example of the condenser fan 60 is shown in FIG. 12 as a centrifugal fan or blower having a housing 84 and motor 86, and other controls. An exit port 88 on the housing 84, is in this embodiment shown as having an exhaust of rectangular shape and dimensioned to fit on the wall 14 at the generally rectangular condenser air discharge grille 32.

A low pressure sensor 90 can be present within an intake to the evaporator blower, and connected electrically with the control board 56. When the pressure is below a predetermined threshold that indicates the filter 24 may be clogged, the circuit board 56 can energize an alarm such as an audible alarm or klaxon, as well as a visible alarm such as a flashing light, to let the worker know to pay attention to the condition of the filter. If the alarm rings, this condition shuts off the power to the heater and/or the air conditioning compressor, for safety purposes. The circuit board 56 is also configure to energize the mechanical air conditioning system, e.g., the compressor 48, or to provide electric current to the heater block 80, depending on the temperature as selected by the user. Preferably, the circuit board 56 keeps the evaporator blower 48 at constant speed, and the same conditions also apply for the speed of the condenser fan 60.

While a favorable arrangement of this invention has been described in reference to a preferred embodiment, it should be understood that the invention is not limited to that precise embodiment. Rather, many modifications and variations will present themselves to those skilled in the art without departing from the scope and spirit of the invention, as defined in the appended claims.

What is claimed is:

1. Mechanical heated/cooled air system for a welding helmet comprising:
   a housing having exterior walls and interior walls defining, in top-to-bottom order, at least an air inlet opening, an evaporator plenum and an equipment compartment within said housing,
   the evaporator plenum communicating with said air inlet opening, the latter being disposed in an exterior wall of the housing, and an evaporator pan within said housing and spaced from said air inlet opening such that the evaporator plenum is defined between said air inlet opening and said evaporator pan;
   an air filter mounted on said air inlet opening;
   an evaporator coil positioned within said evaporator plenum;
   an evaporator fan positioned on said evaporator pan and having an inlet port open to said evaporator plenum and a generally cylindrical outlet port;
   a heater plenum having an inlet positioned on and fitted to the outlet port of said evaporator fan, a heater chamber, and an outlet port positioned on an opening in an exterior wall of said housing;
   a heater module positioned within the heater chamber of said heater plenum;
   a mechanical refrigeration system positioned within the equipment compartment in said housing, including a condenser coil mounted at a condenser air intake opening in an exterior wall of said housing; a compressor having a suction port connected to an outlet port of the evaporator coil and a pressure port connected to an inlet port of said condenser coil; a receiver member connected to an outlet of said condenser coil; and a condenser fan within said equipment compartment having an inlet open to said equipment compartment and an outlet positioned an a condenser air exhaust opening in an exterior wall of said housing;
   wherein a thermally controlled expansion valve is positioned between an outlet of said receiver member and an inlet of said evaporator coil;
   a control portion that controls power output conductors connected with said compressor and to said heater module for selectively energizing one or the other of said compressor and said heater module such that the system provides filtered and heated or cooled air at the outlet port of said heater plenum; and
   a plug-in air hose connector interchangeably positioned at the outlet port of said heater plenum and protruding out of said housing.

2. Mechanical heated/cooled air system for a welding helmet according to claim 1, wherein said air filter mounted on said air inlet opening includes a cylindrical cartridge filter and a self-centering mount affixed atop the housing at said air inlet opening.

3. Mechanical heated/cooled air system for a welding helmet according to claim 2, wherein mount is pyramidical in shape, formed of a plurality of triangular vertical plates and having an apex at its upward end.

4. Mechanical heated/cooled air system for a welding helmet according to claim 1, wherein said air filter includes a protective cover.

5. Mechanical heated/cooled air system for a welding helmet according to claim 1, wherein a pressure switch located in said evaporator plenum is coupled to an alarm circuit, such that a predetermined low pressure in said plenum causes said alarm circuit to generate a clogged-filter alarm signal.

6. Mechanical heated/cooled air system for a welding helmet according to claim 5, wherein said alarm circuit provides both a visual alarm and an audible alarm.

7. Mechanical heated/cooled air system for a welding helmet according to claim 1, wherein said housing is arranged vertically, with said evaporator plenum situated below said inlet port and above said equipment compartment.

8. Mechanical heated/cooled air system for a welding helmet according to claim 1, wherein said housing includes a handle member affixed onto an upper end of said housing and having a transverse grip thereon; and further includes at least a pair of rollers mounted at a lower rear of the housing and a pair of caster wheels at a lower front thereof.

9. Mechanical heated/cooled air system for a welding helmet according to claim 1, wherein said heater plenum inlet and said heater plenum outlet port are each of tubular shape, and said heater plenum is in the form of a box containing said heater module with tapered ends that narrow to said heater plenum inlet and said heater plenum outlet port.

10. Mechanical heated/cooled air system for a welding helmet according to claim 1, wherein said plug-in air hose connector has a plug-in single-hose fitting adapted for attaching a flexible air hose.

11. Mechanical heated/cooled air system for a welding helmet according to claim 1, wherein said plug-in air hose connector has a pair of hose fittings each adapted for connecting to a respective flexible air hose to supply air to two welding helmets.

12. Mechanical heated/cooled air system for a welding helmet according to claim 1, further comprising a control circuit controlling power supplied to said heater module and to said compressor, and configured such that only a selected one of said heater module and said compressor is energized at a given time.

13. Mechanical heated/cooled air system for a welding helmet according to claim 1 wherein said evaporator fan includes a centrifugal blower having a housing situated between said inlet port said generally cylindrical outlet port and said generally cylindrical outlet port is fitted into or onto the inlet of said heater plenum.

14. Mechanical heated/cooled air system for a welding helmet according to claim 1, wherein said housing comprises a removable front panel that can be removed to access all of said evaporator plenum and said equipment compartment.

15. Mechanical heated/cooled air system for a welding helmet according to claim 1, wherein said heater module is electrically powered and has electrical connectors that protrude through said heater plenum.

* * * * *